(12) United States Patent
Yoshida

(10) Patent No.: US 9,664,564 B2
(45) Date of Patent: May 30, 2017

(54) METHOD AND DEVICE FOR MEASURING UNOCCUPIED STATES OF SOLID

(71) Applicant: KYOTO UNIVERSITY, Kyoto-shi, Kyoto (JP)

(72) Inventor: Hiroyuki Yoshida, Uji (JP)

(73) Assignee: KYOTO UNIVERSITY, Kyoto (JP)

( * ) Notice: Subject to any disclaimer, the term of this patent is extended or adjusted under 35 U.S.C. 154(b) by 0 days.

(21) Appl. No.: 14/381,742

(22) PCT Filed: Feb. 26, 2013

(86) PCT No.: PCT/JP2013/054952
§ 371 (c)(1),
(2) Date: Aug. 28, 2014

(87) PCT Pub. No.: WO2013/129390
PCT Pub. Date: Sep. 6, 2013

(65) Prior Publication Data
US 2015/0083907 A1 Mar. 26, 2015

(30) Foreign Application Priority Data

Feb. 28, 2012 (JP) ................................ 2012-042213

(51) Int. Cl.
*G01J 3/30* (2006.01)
*G01J 3/443* (2006.01)
(Continued)

(52) U.S. Cl.
CPC ............... *G01J 3/30* (2013.01); *G01J 3/443* (2013.01); *G01N 23/2251* (2013.01);
(Continued)

(58) Field of Classification Search
CPC ..................................... G01J 3/30; G01J 3/443
See application file for complete search history.

(56) References Cited

U.S. PATENT DOCUMENTS 5,340,976 A 8/1994 Taniguchi et al.
2008/0191137 A1* 8/2008 Poteet et al. ............... 250/338.1
2009/0309023 A1* 12/2009 Page ............................ 250/307

FOREIGN PATENT DOCUMENTS

EP 0 562 874 A1 9/1993
JP A-05-275051 10/1993

OTHER PUBLICATIONS

Jan. 26, 2015 Extended European Search Report issued in European Patent Application No. 13754054.8.
(Continued)

*Primary Examiner* — Nicole Ippolito
*Assistant Examiner* — Sean Luck
(74) *Attorney, Agent, or Firm* — Oliff PLC

(57) ABSTRACT

Intensity of near-ultraviolet light or visible light of 180 to 700 nm emitted from a solid sample, such as an organic semiconductor, irradiated with an electron beam is measured, while kinetic energy (accelerating energy) of the electron beam is changed in a range of 0 to 5 eV so as to obtain a spectrum. Peaks are detected from the spectrum, and the energy thereof is defined as unoccupied-states energy of the sample. The onset energy of the first peak represents electronic affinity energy (electron affinity) of the sample. Since the energy of the electron beam irradiated onto the sample is 5 eV or less, almost no damage is exerted on the sample even when the sample is an organic semiconductor.

20 Claims, 13 Drawing Sheets

(51) Int. Cl.
    G01N 23/225    (2006.01)
    G01N 21/66     (2006.01)
    H01J 37/06     (2006.01)
(52) U.S. Cl.
    CPC .............. *H01J 37/06* (2013.01); *G01N 21/66* (2013.01); *G01N 2223/08* (2013.01)

(56) References Cited

OTHER PUBLICATIONS

Smith N V et al: "Review Article; inverse photoemission," Reports on Progress in Physics, Institute of Physics Publishing, Bristol, GB, vol. 51, No. 9, Sep. 1, 1988 (Sep. 1, 1988), pp. 1227-1294.
Denninger et al., "A VUV Isochromat Spectrometer for Surface Analysis," *App. Phys.*, 1979, vol. 18, pp. 375-380.
Pendry, "New Probe for Unoccupied Bands at Surfaces," *Physical Review Letters*, 1980, vol. 45, No. 16, pp. 1356-1358.
Hill et al., "Charge-separation energy in films of π-conjugated organic molecules," *Chemical Physics Letters*, 2000, vol. 327, pp. 181-188.
Yoshida et al., "Unoccupied electronic states of 3d-transition metal phthalocyanines (MPc: M=Mn, Fe, Co, Ni, Cu and Zn) studied by inverse photoemission spectroscopy," *Journal of Electron Spectroscopy and Related Phenomena*, 2001, vol. 121, pp. 83-91.
Boudaiffa et al., "Resonant Formation of DNA Strand Breaks by Low-Energy (3 to 20 eV) Electrons," *Science*, 2000, vol. 287, pp. 1658-1660.
Erdman et al., "Low-voltage, high-current electron gun," *Rev. Sci Instrum.*, 1982, vol. 53, No. 2, pp. 225-227.
Stoffel et al., "A Low-Energy High-Brightness Electron Gun for Inverse Photoemission," *Nuclear Instruments and Methods in Physics Research*, 1985, vol. A234, pp. 230-234.
Adelt et al., "A low stray light, high current, low energy electron source," *Review of Scientific Instruments*, 1999, vol. 70, No. 10, pp. 3886-3888.
Butler, "Efficient baffles for laser light scattering experiments," *Applied Optics*, 1982, vol. 21, No. 20, pp. 3617-3618.
Akaike et al., "Unoccupied states in copper phthalocyanine/fullerene blended films determined by inverse photoemission spectroscopy," *Organic Electronics*, 2010, vol. 11, pp. 1853-1857.
Ikeda et al., "The Manufacture of Inverse Photoemission Spectroscopy," *Journal of the Vacuum Society of Japan*, 1989, vol. 32, No. 6, pp. 561-565 (with abstract).
Koyasu et al., "Development of an Inverse Photoemission Spectrometer for Electronically Functional Polymer Materials," *The Japan Society of Applied Physics*, 2008, vol. 3, pp. 1096.
Djurovich et al., "Measurement of the lowest unoccupied molecular orbital energies of molecular organic semiconductors," *Organic Electronics*, 2009, vol. 10, pp. 515-520.
Kim et al., "Constructions of Inverse Photoemission Spectrometer and Its Application," *Journal of Korean Chemical Society*, 1996, vol. 40., No. 12, pp. 719-723.
Namatame et al., "Inverse Photoemission," *Journal of the Surface Science Society of Japan*, 1994, vol. 15 No. 8, pp. 507-512.
Sagawa et al., "Gyakko Denshi Bunko," *Oyo Butsuri*, 1986, vo. 55, No. 7, pp. 677-685.
Artamonov et al., "Investigation of unoccupied electron states and determination of the electron affinity of PbS (100) by inverse photoemission spectroscopy," *Semiconductors*, 1993, vol. 27, No. 10, pp. 955-957.
Yoshida et al., "Inverse-hotoemission spectrometer for organic solids," *Abstracts of the Symposium on Molecular Structure*, 1997, pp. 369.
May 21, 2013 International Search Report issued in International Application No. PCT/JP2013/054952.
May 21, 2013 Written Opinion issued in International Application No. PCT/JP2013/054952 (with translation).

* cited by examiner

Fig. 8A
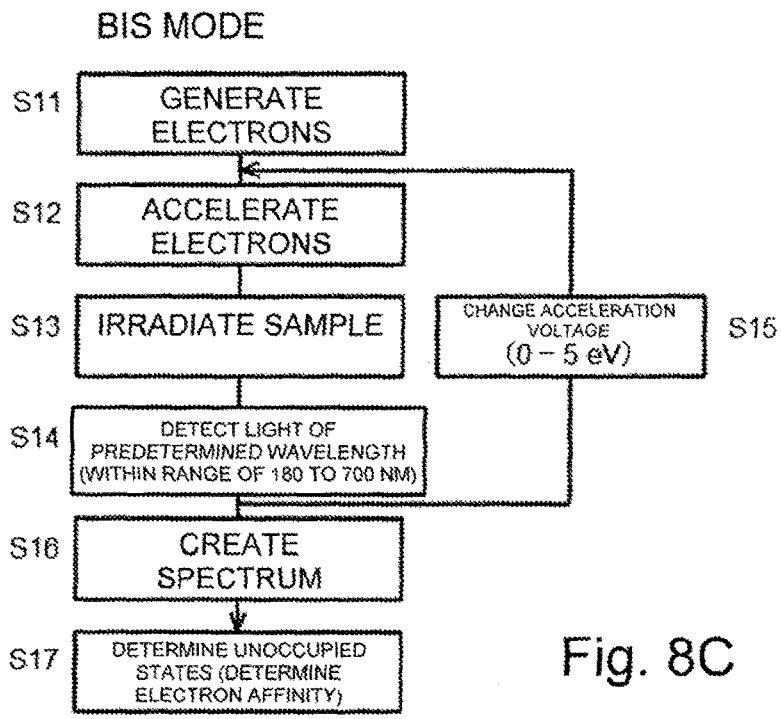
Fig. 8B
Fig. 8C
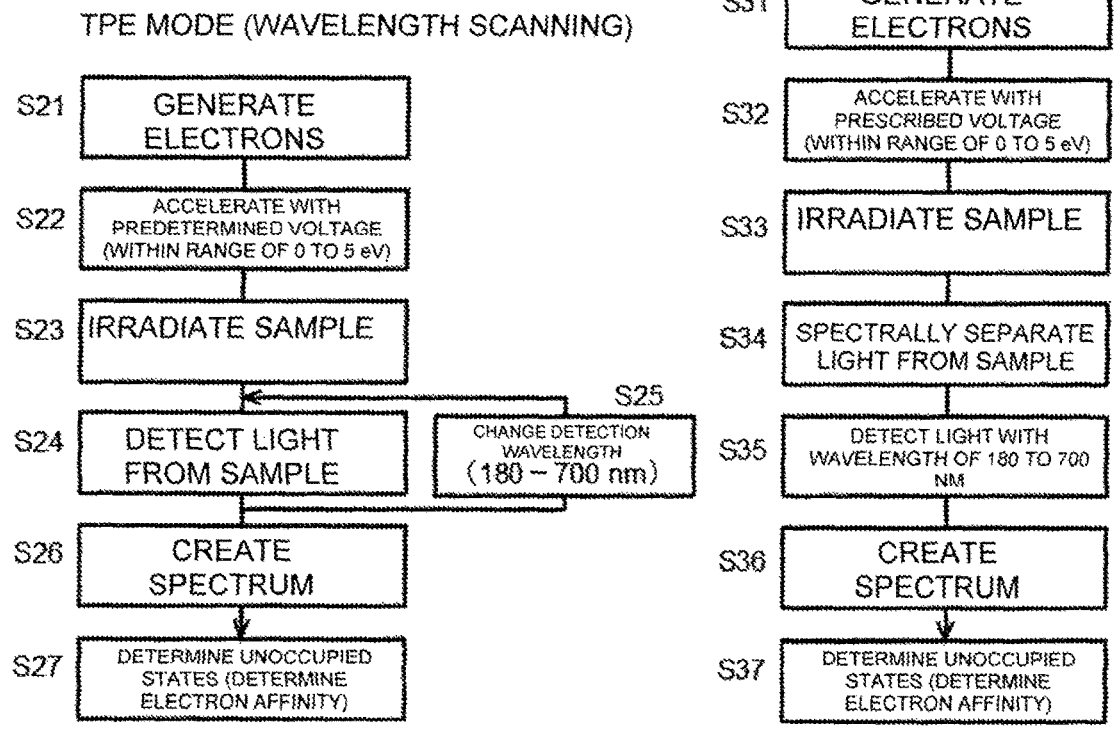

TPE mode (Ek = 1.18 eV)

METHOD AND DEVICE FOR MEASURING UNOCCUPIED STATES OF SOLID

TECHNICAL FIELD

The present invention relates to a method and device which are effective in measuring values of unoccupied states of solids, such as semiconductors and metals, and organic semiconductors in particular.

BACKGROUND ART

Organic semiconductor devices are attracting attention as a next-generation semiconductor device because thin film fabrication can be conducted at low costs, unique characteristics such as mechanical flexibility are retained, and materials themselves of the organic semiconductor devices can easily be modified by an organic synthetic technology. Display devices with use of organic light emitting diodes (OLEDs) have already been put in practical use, and organic field effect transistors (OFETs) as a drive device for flexible display devices and/or organic photovoltaic cells (OPVs) are being studied toward practical application.

In such organic semiconductors, a hole having positive charge and an electron having negative charge render semiconductor their characteristics. It is possible, until now, to accurately determine the valence states, which relate to the hole conduction, by photoemission spectroscopy and/or photoemission yield spectroscopy. On the contrary, since there is no method for accurately determine unoccupied states, that are electron conduction levels, the behavior of electrons in organic semiconductors is not yet fully known. Under these circumstances, a device for accurately measuring the unoccupied states of the organic semiconductors is needed.

To easily measure the unoccupied states of the organic semiconductors, methods as shown below are used: (1) a method for estimating an electron affinity, which is the lower end energy of the unoccupied-states, based on a reduction potential obtained by an electrochemical approach (cyclic voltammetry) in solution; and (2) a method for estimating the lower end energy of the unoccupied-states by adding a band gap calculated from an optical absorption spectrum to an ionization energy (which corresponds to the upper end energy of the HOMO level) determined by photoemission spectroscopy.

However, in the case of the electrochemical method (1), the reduction potential of molecules in solution is often largely different from the electron affinity in solid, which makes measured values inaccurate. In the case of the method (2), the band gap obtained from the optical absorption spectrum is often smaller than an actual gap due to the influence of excitons. In systems having a large electron correlation such as molecular systems, injected and released charges and remaining electrons have a large correlation. As a consequence, the method (2) has a problem that correct unoccupied-states energy cannot be obtained.

As another method for measuring the unoccupied states, inverse photoemission spectroscopy which is a time inversion process of photoemission spectroscopy is also known. In the inverse photoemission spectroscopy, a sample is irradiated with an electron beam with uniform energy, and light emitted thereby is detected, so that density of states of the unoccupied-states can be examined. Based on this spectrum, in particular, electron affinity of solids, which is an index of the unoccupied states, can be obtained. In principle, this method is considered to provide most reliable values (Non Patent Literature 1 to Non Patent Literature 4).

CITATION LIST

Non Patent Literature

[Non Patent Literature 1] Denninger, G., V. Dose, et al., "VUV ISOCHROMAT SPECTROMETER FOR SURFACE-ANALYSIS." Appl. Phys. 18, 375-380 (1979)
[Non Patent Literature 2] Pendry, J. B., "NEW PROBE FOR UNOCCUPIED BANDS AT SURFACES", Phys. Rev. Lett. 45, 1356-1358 (1980)
[Non Patent Literature 3] Hill, I G; Kahn, A; Soos, Z G; Pascal, R A, "Charge-separation energy in films of pi-conjugated organic molecules". Chem. Phys. Lett. 327, 181-188 (2000)
[Non Patent Literature 4] Yoshida, H.; Tsutsumi, K.; Sato, N., "Unoccupied electronic states of 3d-transition metal phthalocyanines (MPc: M=Mn, Fe, Co, Ni, Cu and Zn), studied by inverse photoemission spectroscopy", J. Elect. Spectrosc. Relat. Phenom. 121, 83-91 (2001)
[Non Patent Literature 5] Boudaiffa, Cloutier, Hunting, Huels, Sanche, "Resonant Formation of DNA Strand Breaks by Low-Energy (3 to 20 eV) Electrons", Science 287, 1658 (2000)
[Non Patent Literature 6] Erdman, P. W. and E. C. Zipf (1982). "LOW-VOLTAGE, HIGH-CURRENT ELECTRON-GUN." Review of Scientific Instruments 53(2): 225-227
[Non Patent Literature 7] Stoffel, N. G. and P. D. Johnson (1985). "A LOW-ENERGY HIGH-BRIGHTNESS ELECTRON-GUN FOR INVERSE PHOTOEMISSION." Nuclear Instruments & Methods in Physics Research Section a-Accelerators Spectrometers Detectors and Associated Equipment 234(2): 230-234
[Non Patent Literature 8] M. Adelt, R. Koerber, W. Drachsel, and H.-J. Freund, "A low stray light, high current, and low energy electron source" Rev. Sci. Instrum. 70, 3886-3888 (1999)
[Non Patent Literature 9] J. E. Butler, "Efficient baffles for laser light scattering experiments", Applied Optics 21, 3617-3618 (1982)

SUMMARY OF INVENTION

Technical Problem

In the inverse photoemission spectroscopy, a sample is irradiated with an electron beam. Since signal intensity is weak, a large amount of electron irradiation is necessary. In the conventional inverse photoemission spectroscopy, a sample was irradiated with an intense electron beam of about 10 eV, and therefore when measurement of an organic sample was performed, there was a problem that the sample is damaged by the electron bombardment.

Moreover, in order to observe a signal at a highest possible efficiency, a bandpass detector is used for detecting photons. The bandpass detector uses the phenomenon that calcium fluoride, strontium fluoride or other similar substance does not transmit light having 10 eV or higher energy. At the same time, as the detector having sensitivity at 9 eV or more, a Geiger-Mueller tube that uses iodine, acetone, or other gases as the detection gas, or an electron multiplier having sensitivity enhanced by NaCl are combined so as to attain a bandpass characteristic of about 10 eV. These characteristics of the bandpass detector is based on the light transmission characteristic of the filter and/or based on the ionization characteristic of detection gas, which limits its energy resolution to 0.4 to 0.8 eV. In addition, the photo response characteristic is significantly asymmetrical to the energy. Accordingly, a measured spectrum has low resolution, which makes it difficult to measure unoccupied states with an adequate accuracy required in other fields such as development of organic semiconductors.

The problem to be solved by the present invention is to provide a method and device for measuring unoccupied states of solids, including not only semiconductors but also metals and non-conductors, with high resolution and without damaging a sample.

Solution to Problem

In order to solve the aforementioned problems, a first aspect of a method for measuring unoccupied states of a solid according to the present invention includes:
 a) a step of generating an electron beam;
 b) a step of changing kinetic energy of the generated electron beam within a range of 0 to 5 eV and irradiating a solid sample with the electron beam;
 c) a step of measuring intensity of light of a predetermined wavelength within a range of 180 to 700 nm included in electromagnetic waves emitted from the solid sample; and
 d) a step of determining unoccupied-states energy of the solid sample based on a spectrum created by the intensity of light with respect to the kinetic energy of the electron beam.

In the method of the first aspect (which is referred to as a BIS mode), intensity of light (partially including near-ultraviolet light) emitted from a solid sample irradiated with an electron beam is measured, while kinetic energy (accelerating energy) of the electron beam is changed. As a result, a spectrum having electron beam energy as an abscissa and the intensity of light as an ordinate is created. The spectrum includes peaks, which correspond to the unoccupied states of the unoccupied states of the solid sample. In the above-described step of determining unoccupied-states energy, peaks are detected from the spectrum and their energy is defined as the unoccupied-states energy. Particularly, the difference in energy between the onset of the first peak and the vacuum level represents electronic affinity energy (electron affinity) of the solid sample.

It should be noted that the vacuum level of the solid can be measured by conventionally known methods. For example, as shown in FIG. 13A, the vacuum level can be determined based on the rising energy of an electron beam. A high-sensitive amperemeter A, such as picoammeters, is connected to a sample S, and the amount of electrons flowing through the substrate is measured as the function of the accelerating energy. FIG. 13B and FIG. 13C are graphs in which a sample current flowing through an Ag sample is plotted with respect to the acceleration energy of the electron. As seen in these graphs, the curve of sample current rises at certain value of the energy, and the inflection point (=local maximum of primary differential=a point where secondary differential is 0) is defined as an origin of the acceleration energy of the electron. Adding to this origin of electron acceleration energy the central energy of the bandpass filter used in a measurement makes the "vacuum level."

Another conventional method for determining the vacuum level involves photoemission spectroscopy. In this method, photoemission spectroscopy of the same sample is conducted at the same time, and cutoff energy of a secondary electron of the spectrum is obtained. Adding excitation light energy to the cutoff energy, the vacuum level is obtained.

The wavelength of the light to be measured is set to 180 to 700 nm because electron affinity values of many organic semiconductors are within this range as shown in FIG. 14. Although only organic semiconductors, such as PTCDA, $F_{16}$—CuPc, $C_{60}$, PCBM, CuPc, ZnPc, pentacene, and P3HT, are shown in FIG. 14, electron affinity of inorganic semiconductors and metals may also generally be determined by detecting the light having the wavelengths in this range.

In the step of measuring an intensity of light, a configuration of using a bandpass filter having a transmission range of 180 to 700 nm and measuring the intensity of light that passes the bandpass filter may be adopted.

In place of the bandpass filter, a spectrometer with an exit slit that select the aforementioned wavelength band may be used.

In order to solve the aforementioned problems, a second aspect of a method for measuring unoccupied states of a solid according to the present invention includes:
 a) a step of generating an electron beam;
 b) a step of accelerating the generated electron beam with a predetermined energy within a range of 0 to 5 eV and irradiating a solid sample with the electron beam;
 c) a step of spectrally separating light within a range of 180 to 700 nm included in electromagnetic waves emitted from the solid sample and measuring intensity of each wavelength to generate a spectrum; and
 d) a step of determining unoccupied-states energy of the solid sample based on the spectrum.

In the method of the second aspect (which is referred to as the TPE mode), a spectrum is obtained in the step of generating a spectrum, with the wavenumber of the measured light as an abscissa and the light intensity as an ordinate. The spectrum includes peaks. In the step of determining unoccupied-states energy, the peaks are detected from the spectrum and their energy is defined as unoccupied-states energy. Particularly, a difference in energy between a rising part of the first peak and a vacuum level represents electronic affinity energy (electron affinity) of the solid sample.

In the step of generating a spectrum, a method may be adopted in which a spectrometer, an exit slit, and a photon detector are used, and a position (angle) of the spectroscope (typically a grating or a prism) is changed to change the wavelength of the light passing through the exit slit so as to generate a spectrum.

It is also possible to adopt a method in which each wavelength of spectrally separated light is measured all at once with a linear sensor such as CCD without changing the position of the spectroscope.

In order to solve the aforementioned problems, a first aspect of a device for measuring unoccupied states of a solid according to the present invention includes:
 a) an electron beam generator;
 b) an electron beam accelerator for changing kinetic energy of the generated electron beam within a range of 0 to 5 eV and irradiating a solid sample with the electron beam;
 c) a light intensity measuring unit for measuring intensity of light of a predetermined wavelength within a range of 180-700 nm included in electromagnetic waves emitted from the solid sample; and
 d) an unoccupied states determiner for determining unoccupied-states energy of the solid sample based on a spectrum created by the intensity of light with respect to the kinetic energy of the electron beam.

The light intensity measuring unit may be made of a bandpass filter having a transmission range of 180 to 700 nm and a photon detector that measures intensity of light that passes the bandpass filter.

In place of the bandpass filter, a spectrometer and an exit slit may be used.

In order to solve the aforementioned problems, a second aspect of a device for measuring unoccupied states of a solid according to the present invention includes:

a) an electron beam generator;

b) an electron beam accelerator for accelerating an electron beam generated by the electron beam generator with a predetermined energy within a range of 0 to 5 eV and irradiating a solid sample with the electron beam;

c) a spectrum generator for generating a spectrum by spectrally separating light within a range of 180 to 700 nm included in electromagnetic waves emitted from the solid sample and measuring intensity of the light as a function of wavelength; and d) an unoccupied states determiner for determining unoccupied-states energy of the solid sample based on the spectrum.

As the spectrum generator, a spectrophotometer including a spectroscope, a spectroscope drive mechanism that changes the position (angle) of the spectroscope, an exit slit, and a photon-detector may be used.

It is also possible to use a spectrograph that measures each wavelength of spectrally separated light all at once with a linear sensor such as CCDs without changing the position of the spectroscope.

Advantageous Effects of Invention

In the conventional methods, a sample was irradiated with an electron beam with energy close to 10 eV. This caused a problem that the sample to be measured was deteriorated or damaged, so that correct values could not be obtained. However, in the methods according to the present invention, a solid sample to be measured is irradiated with an electron beam of only 5 eV or less, so that deterioration and damage of a solid sample, and an organic semiconductor samples in particular, can be suppressed (see Non Patent Literature 5). Furthermore, the light emitted from the sample was vacuum ultraviolet light (10 to 200 nm) in the conventional inverse photoemission spectroscopy, whereas in the methods according to the present invention, electron beam energy is lowered so that near-ultraviolet light or visible light (180 to 700 nm) is detected. This makes it possible to use optical materials, such as synthetic quartz (for example, lens and windows), high-resolution bandpass light filters, and high efficient photomultipliers. Moreover, since the detection light is hardly absorbed by oxygen ($O_2$), photon detection can be performed in atmospheric air, which simplifies device configuration. As a result, device resolution becomes 2 to 3 times higher than before.

It should be noted that the method according to the present invention is theoretically applicable to non-conductor samples. However, in the case of non-conductor samples, special sample settings, such as minimizing the sample thickness, is needed to prevent a charge accumulation (charge up) due to electrons, which come from an electron gun, and to let the charges flow out as current.

BRIEF DESCRIPTION OF DRAWINGS

FIG. 7A, FIG. 7B, and FIG. 7C are schematic configuration diagrams showing the configuration of various devices for performing the methods according to the present invention, in which FIG. 7A shows an example of using a bandpass filter and a photomultiplier, FIG. 7B shows an example of using a spectrometer and a photomultiplier, and FIG. 7C shows an example of using a spectrograph and a linear sensor.

FIG. 8A, FIG. 8B, and FIG. 8C are flowcharts of various embodiments for implementing the methods according to the present invention, in which FIG. 8A shows the BIS mode, FIG. 8B shows the TPE mode to scan wavelengths, and FIG. 8C shows the TPE mode with use of a linear sensor.

FIG. 12A, FIG. 12B, and FIG. 12C are schematic configuration diagrams of various devices for collecting the light from a sample, in which FIG. 12A shows a reflection method, FIG. 12B shows a paraboloidal mirror light collection method, and FIG. 12C shows an ellipsoidal mirror light collection method.

DESCRIPTION OF EMBODIMENTS

A method and device (BIS mode) according to a first aspect of the present invention was used to measure unoccupied states of copper phthalocyanine CuPc which is a kind of typical organic semiconductors.

[Device and Method for Measurement]

Figure 1:
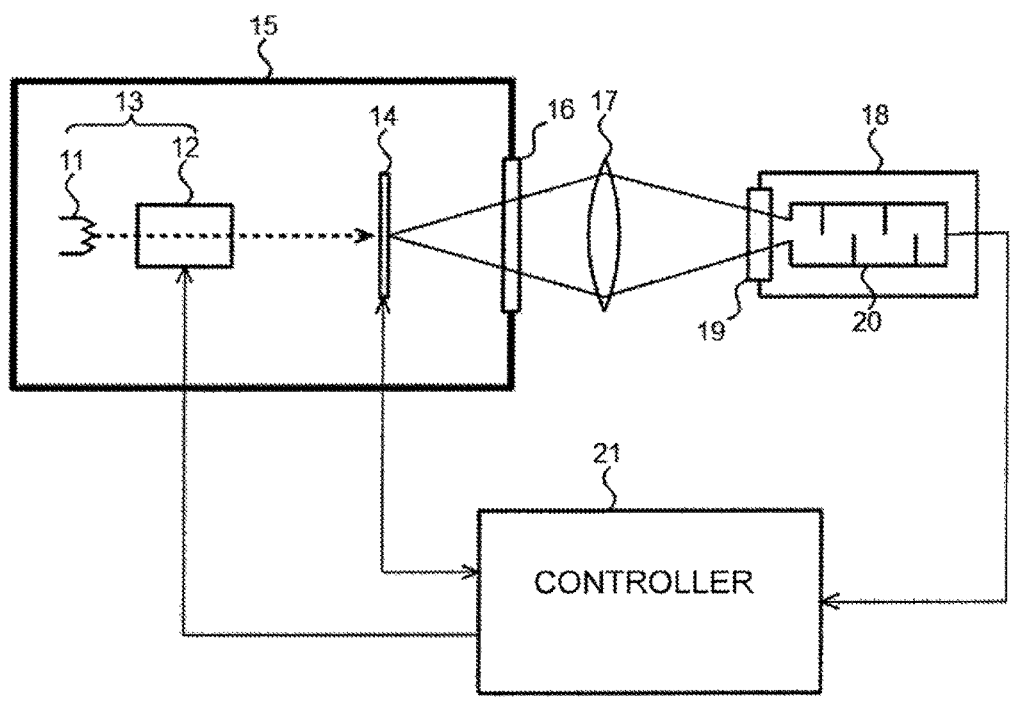
FIG. 1 is a schematic configuration diagram showing a device for measuring unoccupied states of a solid as one embodiment of the present invention.

The outline of the measuring device is shown in FIG. 1. A heat cathode 11, an electron lens 12 (these two components constitute an electron gun 13), and a sample 14 are placed in a vacuum chamber 15, and the vacuum chamber 15 is maintained in ultra-high vacuum (pressure of $10^{-6}$ Pa or less). The sample 14 is irradiated with electrons having uniform energy by the electron gun 13. Electromagnetic waves emitted from the sample 14 are extracted to the outside through a window 16 provided on the vacuum chamber 15 and are collected into a photon detector 18 via a convex lens 17. In the device according to the present invention, the light in the range of ultraviolet or near-ultraviolet is measured, so that the window 16 and the lens 17 of the vacuum chamber 15 may be made of quartz.

The photon detector 18 consists of a bandpass filter 19 and an electron multiplier (photomultiplier) 20. Only the light of a specific wavelength included in the electromagnetic waves emitted from the sample 14 passes the bandpass filter 19, and is detected by the photomultiplier 20 with high sensitivity. As the bandpass filter 19, a commercially available product having a transmission center wavelength of 180 to 700 nm (for example, bandpass filters made by Semrock, Inc. in USA, and bandpass filters made by Asahi Spectra Co., Ltd) may be used. Today, commercially available bandpass filters in this wavelength range have a full-width at half maximum of about 10 to 20 nm.

As the heat cathode 11 for use in the electron gun 13, various metals, oxides, and the like may be used, and barium oxide BaO may preferably be used in particular. The reasons thereof include: (1) operating temperature of BaO is lower than other cathodes (absolute temperature of about 1150 K), so that its energy resolution is higher (the resolution in full-width at half maximum is about 0.25 eV); (2) density of extractable current is high; and (3) easy availability (inexpensive products with stable performance are available since the BaO heat cathode was used to be used as an electron gun for cathode-ray tubes of television sets). In this device, a product made by Kimball Physics Inc. in USA was used.

Two types of low-energy electron sources are commonly used for the device according to the present invention:

(1) Erdman-Zipf type: see Non Patent Literature 6; and
(2) Stoffel-Johnson type: see Non Patent Literature 7.

It was confirmed that the sources of both the types may be applied to this device.

An electron acceleration voltage of the electron gun 13 is controlled by a controller 21. The controller 21 also controls the amount of electrons (current) emitted from the electron gun 13 and the irradiation area of the sample 14, by which the current density on the irradiation surface on the sample 14 is also controlled. An appropriate current density is about $10^{-3}$ to $10^{-8}$ A/cm$^2$. When the current density is larger than this range, the current spreads out due to Coulomb repulsion of electrons, whereas when the current density is smaller, it becomes hard to detect the light from the sample.

The controller 21 measures the intensity (number of photons) of the electromagnetic waves detected with the photon detector 18 while gradually changing the electron acceleration voltage of the electron gun, and standardizes the intensity with the amount of emitted electrons (current amount) to prepare a spectrum (inverse photoemission spectrum).

Figure 13A:
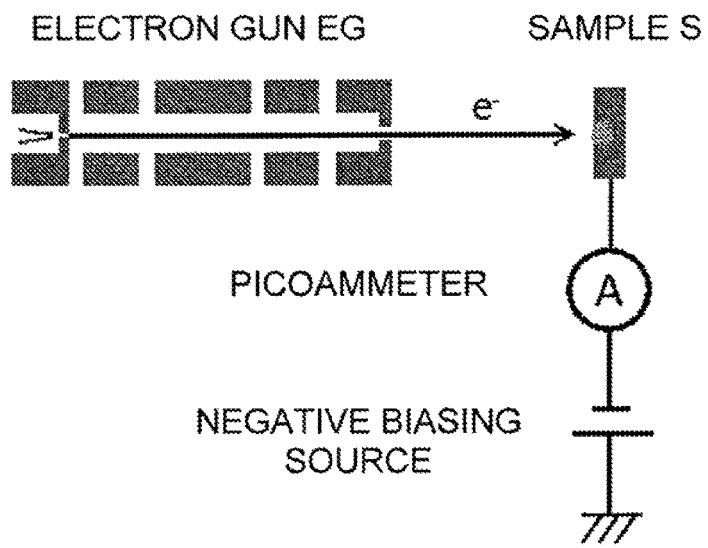
FIG. 13A is a schematic configuration diagram of a device for measuring a vacuum level of a solid.
Figure 13B:
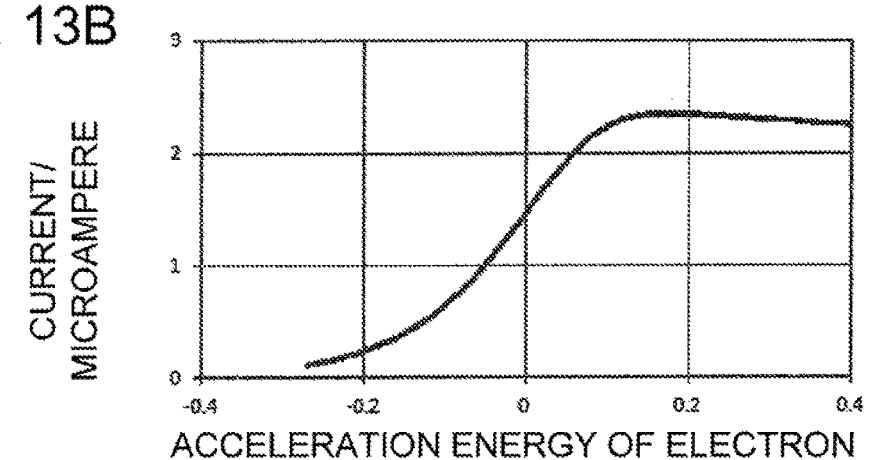
FIG. 13B and FIG. 13C are graphs showing measurement results with Ag as a sample.
Figure 13C:
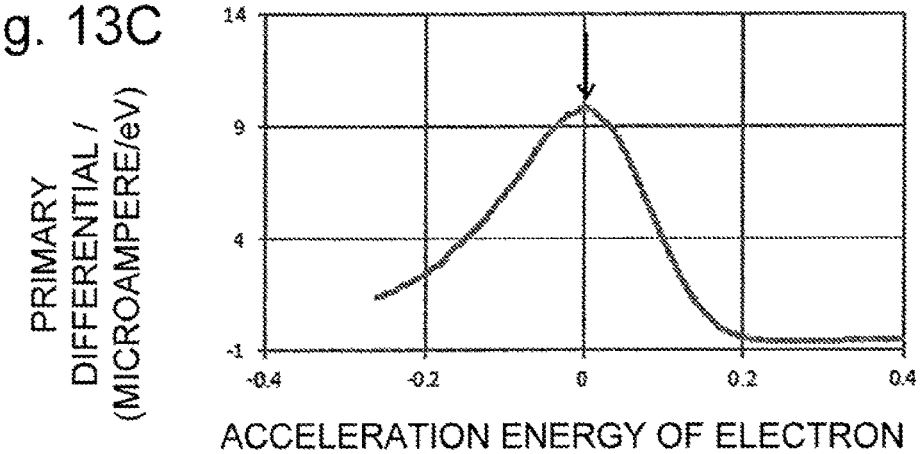
Figure 14:
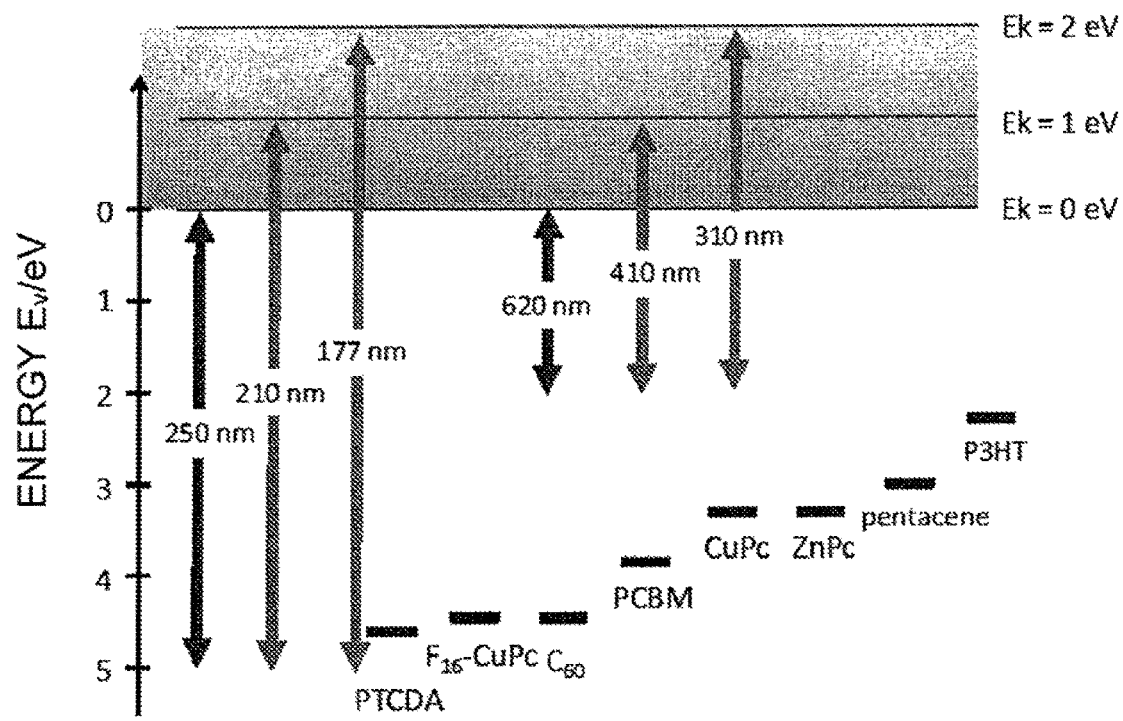
FIG. 14 is an energy diagram showing the electron affinity of various organic semiconductors.

In actuality, it is preferable to apply negative bias voltage to the sample 14 to generate a low-energy electron beam of 5 eV or less so as to achieve efficient convergence (FIG. 13A). For example, when the sample 14 is irradiated with an electron beam of 15 eV to apply −10 V to the sample 14, it is equivalent to irradiation of electrons of 5 eV. In this case, the accelerating energy (kinetic energy) of the electrons irradiated onto the sample 14 can be swept by the following two methods:

(1) A method of sweeping the kinetic energy (accelerating energy) of the electrons emitted from the electron gun; and
(2) A method of keeping the kinetic energy of the electrons from the electron gun constant and sweeping the bias voltage applied to a sample substrate.

It was confirmed that both the methods are applicable to this device.

[Characteristics of Photon Detector]

Figure 2:
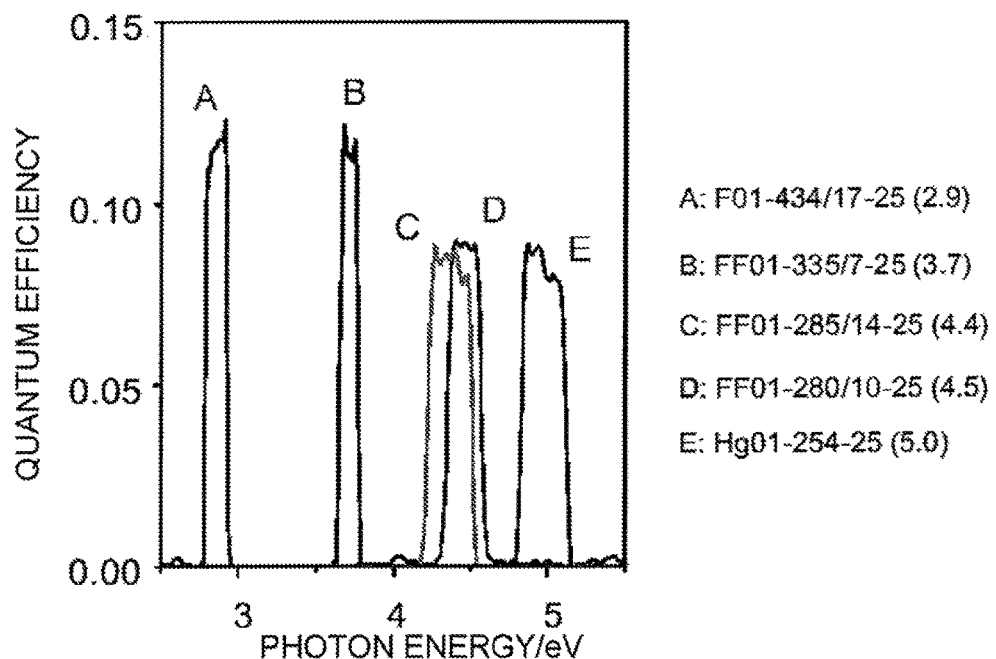
FIG. 2 is a graph showing sensitivity characteristics of a photon detector used in the measuring device of the embodiment in the case where various bandpass filters are used.
Figure 3A:
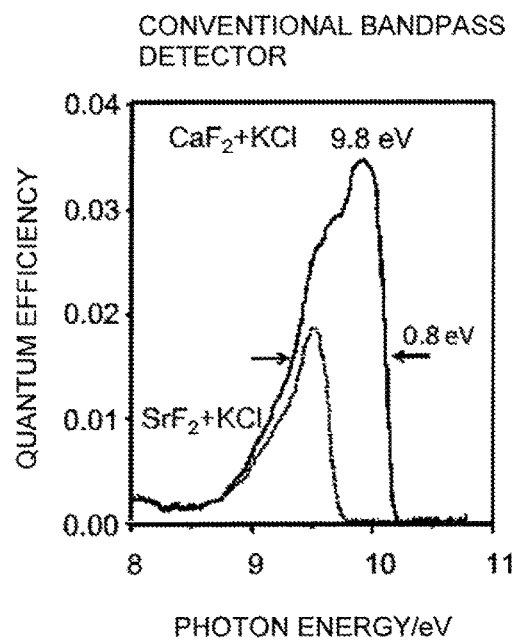
FIG. 3A and FIG. 3B are graphs showing sensitivity curves of a conventional bandpass detector with use of a calcium fluoride $CaF_2$ or strontium fluoride $SrF_2$ filter with KCl coated electron multiplier, and of a bandpass filter with a photomultiplier used in the present embodiment, respectively.

FIG. 2 shows sensitivity characteristics of the photon detector 18. This graph shows sensitivity characteristics of the photon detector 18 in the case where the bandpass filter 19 is replaced with filters having various transmission properties. The bandpass filters (A to E) described herein are all made by Semrock, Inc. As shown in FIG. 3A, the conventionally used bandpass detectors have a center wavelength of about 10 eV. When calcium fluoride CaF$_2$ is used, resolution is generally 0.8 eV. When strontium fluoride SrF$_2$ is used, the resolution increases up to 0.4 eV, though detection sensitivity is substantially degraded thereby. These sensitivity curves are peculiar to each substance and are unchangeable.

Figure 3B:
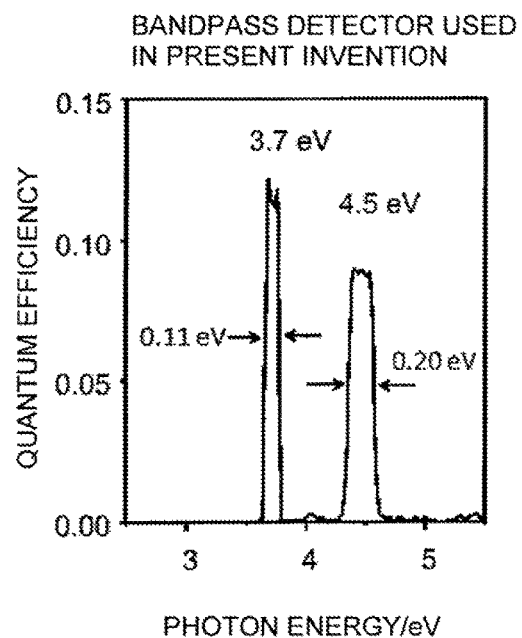

Contrary to this, in the case of the photon detector used in the present invention, the sensitivity characteristics can be adjusted by arbitrarily selecting bandpass filters having a center wavelength of 180 nm to 700 nm and resolution of 0.01 to 0.5 eV as described before (FIG. 3B).

Figure 4:
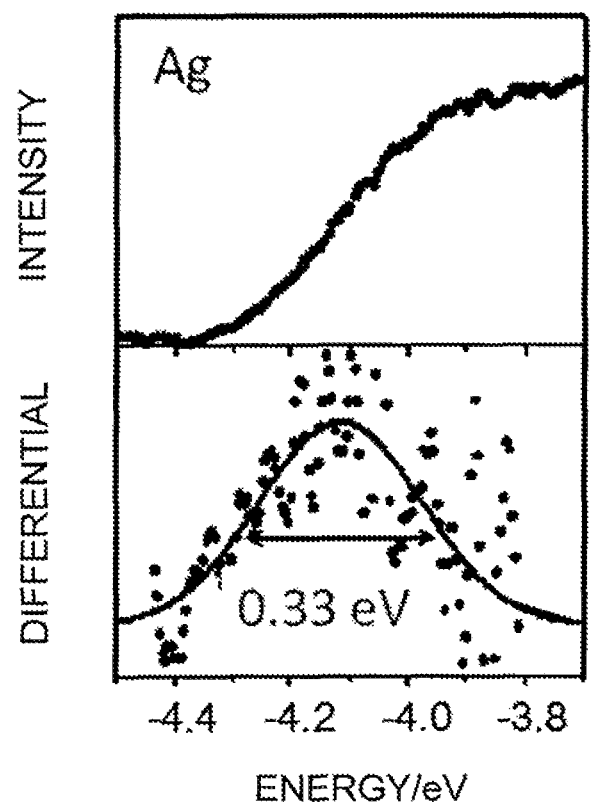
FIG. 4 shows upper and lower graphs in the case where a bandpass filter having resolution of 0.20 eV is used for measurement of energy resolution of the photon detector used in the embodiment, the upper graph showing a result of measuring the intensity of light from silver Ag in the vicinity of the Fermi edge of 4.15 eV and the lower graph showing a primary differential of the result.

The overall energy resolution by the photon detector 18 in this measuring device was measured with silver Ag as a sample. FIG. 4 shows, on the upper graph, the intensity of light from silver Ag in the vicinity of a Fermi edge of 4.15 eV in the case where a bandpass filter having resolution of 0.20 eV is used, and, on the lower graph, shows a primary differential of the spectrum. In this case, it was found out that energy resolution of 0.33 eV can be obtained by the photon detector 18 as a whole. Similarly, when a filter with resolution of 0.29 eV was used as the bandpass filter 19, energy resolution of 0.37 eV was obtained, and when the bandpass filter 19 with resolution of 0.11 eV is used, the resolution of the device is estimated to be 0.27 eV.

While the above-stated filters were selected in order to balance the sensitivity and the resolution, it is also possible to obtain bandpass filters with higher resolution. These filters have a transmittance as high as 65 to 80%, and the transmittance is substantially constant in a transmission wavelength region. As a result, both the high resolution and sensitivity can be achieved.

[Measurement Results of Organic Semiconductors]

Figure 5:
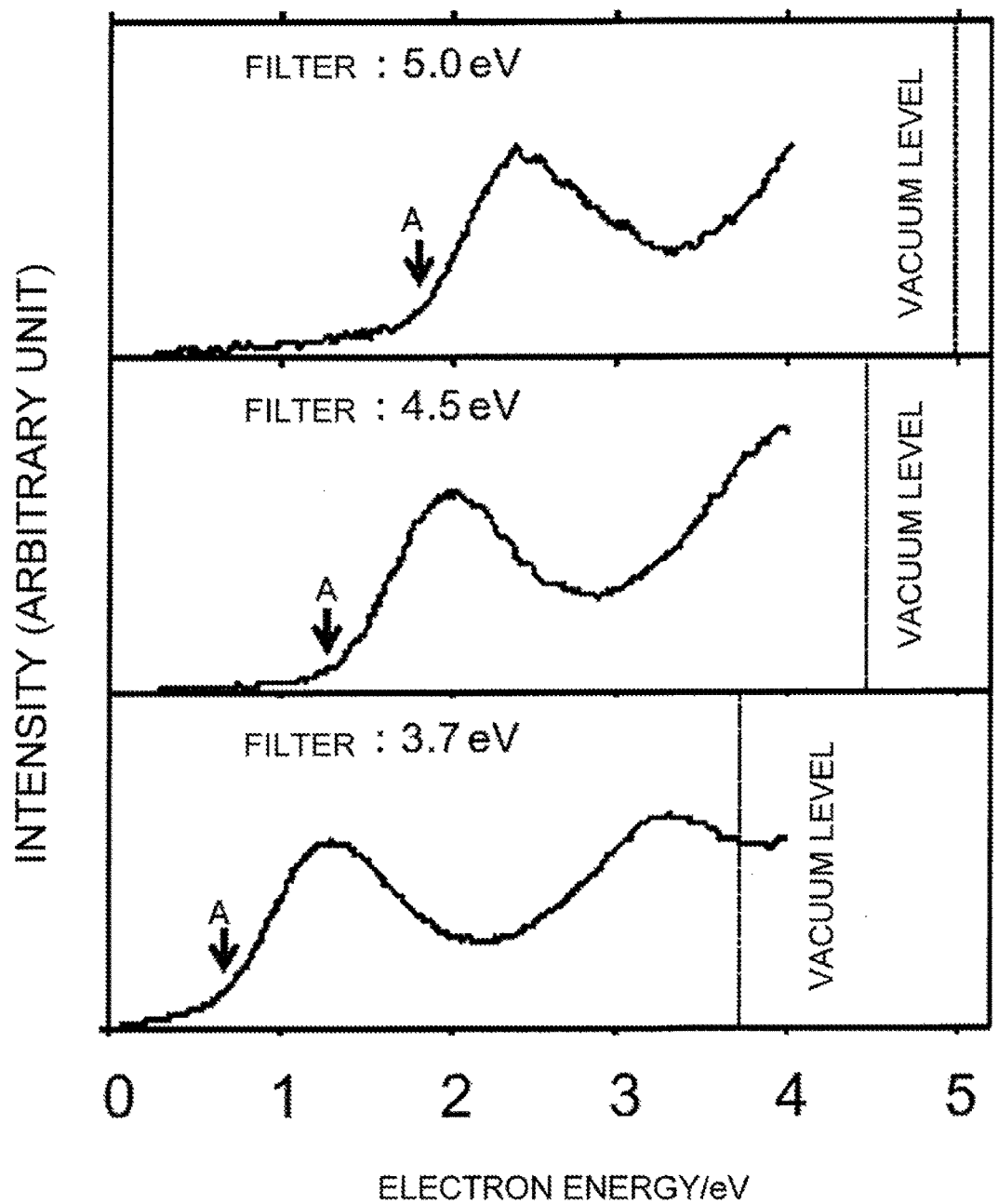
FIG. 5 is a graph showing the result of measuring unoccupied states of copper phthalocyanine CuPc by using the device of the embodiment.

The result of measuring unoccupied states of copper phthalocyanine CuPc by using the above-configured device is shown in FIG. 5. The upper row shows a measurement result when a bandpass filter with a center wavelength of 5.0 eV (≈250 nm) is used, the middle row shows a measurement result when a bandpass filter with a center wavelength of 4.5 eV (≈280 nm) is used, and the lower row shows a measurement result when a bandpass filter of 3.7 eV (≈335 nm) is used. When the center wavelength of the bandpass filter is changed, the spectrum shifts in proportion to the change. This proves that the unoccupied states of copper phthalocyanine CuPc is correctly measured by this measurement.

Since the resolution is higher as compared with the spectrum measured by the conventional method, a onset (point A) of the spectrum is clearly identified. Based on the onset, the electron affinity of copper phthalocyanine CuPc could be determined to be 3.1±0.1 eV.

The entire spectrum can be measured by using an electron beam of 5 eV or less. For determination of the electron affinity, only the energy of the onset of the spectrum is necessary, and therefore measurement can be performed with an electron beam of 1 eV or less. Thus, measurement with a low-energy electron beam can effectively prevent the sample from being damaged by irradiation of the electron beam.

[Damage of Sample]

Figure 6A:
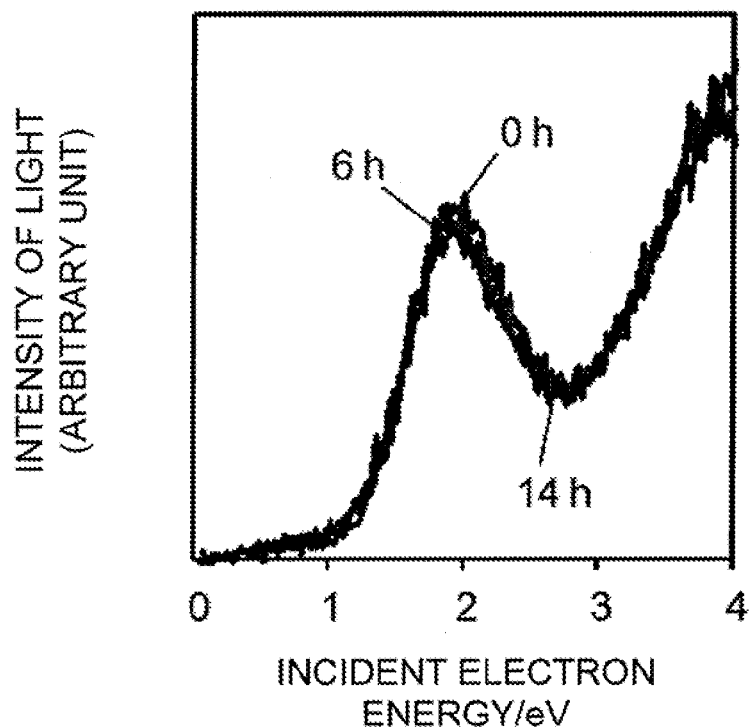
FIG. 6A and FIG. 6B are graphs showing damage of a copper phthalocyanine CuPc sample caused by measurement performed by a method according to the present invention (BIS mode where incident electron energy is 0 to 4 eV and current is 1.4 μA) and those observed after the electron bombardment of 10, 30 and 60 minutes, the condition of which is similar to the conventional method (incident electron energy is 10 eV and current is 1.4 μA), respectively.
Figure 6B:
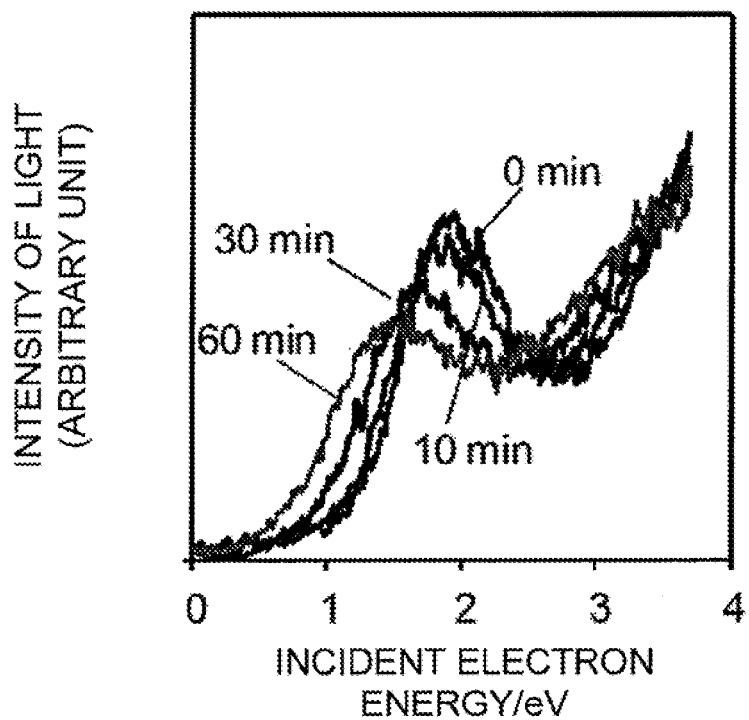

Experiments were conducted to examine damage of the sample caused by measurement. FIG. 6A is a graph representing relationship between electron irradiation time (0 h, 6 h, and 14 h) and detected spectra when unoccupied states of copper phthalocyanine CuPc is measured by the method (BIS mode) according to the present invention. FIG. 6B is a graph representing a spectrum detected when the electron irradiation time is set to 0 min, 10 min, 30 min, and 60 min on the electron irradiation condition same as those in the conventional method (electron energy of 10 eV). The electron current was set to 1.4 µA in both the cases.

As shown in FIG. 6A, any large change in the shape of the spectrums was not observed when measurement was performed after irradiation with an electron beam of 1.4 µA for 14 hours or more in the measuring method according to the present invention. Contrary to this, in the conventional measurement, damage by the irradiation of an electron beam was observed in only 10 minutes as shown in FIG. 6B. In one hour that is normal measurement time, a clear change was observed, that is, the shape of the peak collapsed and the spectrum shifted to a low energy side, indicating that correct electron affinity could not be obtained. Although copper phthalocyanine CuPc is known to be resistant to electron irradiation, it is evident that reliable measurement is difficult due to the damage caused by electron irradiation even in the case of using such copper phthalocyanine CuPc. On the contrary, in the method according to the present invention that uses a slow-speed electron beam, damage of copper phthalocyanine CuPc by the electron beam is negligible.

[Examples of Other Device Configuration]

Figure 7A:
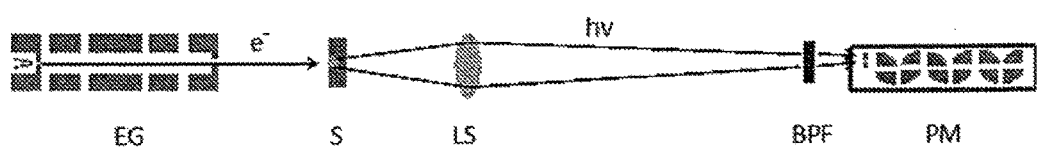
Figure 7B:
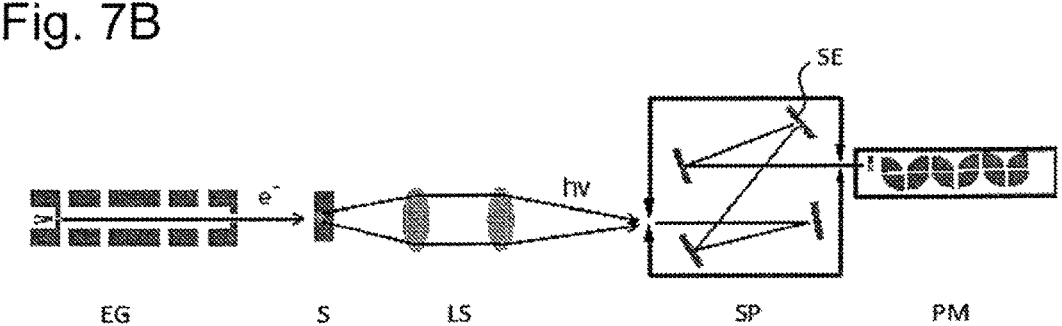

While the examples in which the bandpass filter BPF and the photomultiplier PM are used as a photon detector in the BIS mode have been described in the foregoing, the method according to the present invention is not limited to such a configuration, and may be performed in various device configurations. For example, as shown in FIG. 7B, the photon detector may be made of a photomultiplier PM and a spectrometer SP. For comparison, the photon detector of FIG. 1 is shown in FIG. 7A in this configuration. When the configuration of FIG. 7B is used in the BIS mode, the position (angle) of a spectrum element SE of the spectrometer SP is fixed so that the light of a predetermined wavelength passes through an exit slit and enters into the photomultiplier PM, and electron energy delivered onto the sample S from the electron gun EG is changed. The flowchart for this method (and the measuring method performed with the device configuration of FIG. 7A) is shown in FIG. 8A. In FIG. 7B, LS denotes a lens for collecting the light, which is emitted from the sample S, into an entrance slit of the spectrometer SP. The LS may be made of optical fiber. This also applies to FIG. 7A and later-described FIG. 7C.

The configuration of FIG. 7B can also be used in the TPE mode. In this case, by changing the position (angle) of the spectrum element SE of the spectrometer SP, the wavelength of the light passing through the exit slit and entering into the photomultiplier PM is scanned. The flowchart for this method is shown in FIG. 8B.

Figure 7C:
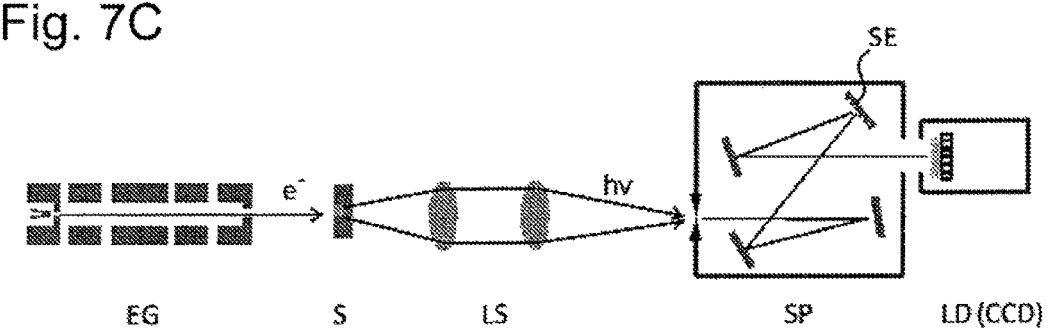

FIG. 7C shows an example in which the photon detector is made of a spectrograph and a linear sensor LD. Although a CCD can typically be used as the linear sensor LD, other light receiving elements arrayed in a wavelength dispersion direction may also be used. This configuration is used in the TPE mode. In the case of this device configuration, the spectrally separated wavelengths are measured all at once with the linear sensor as shown in the flowchart of FIG. 8C.

Figure 9A:
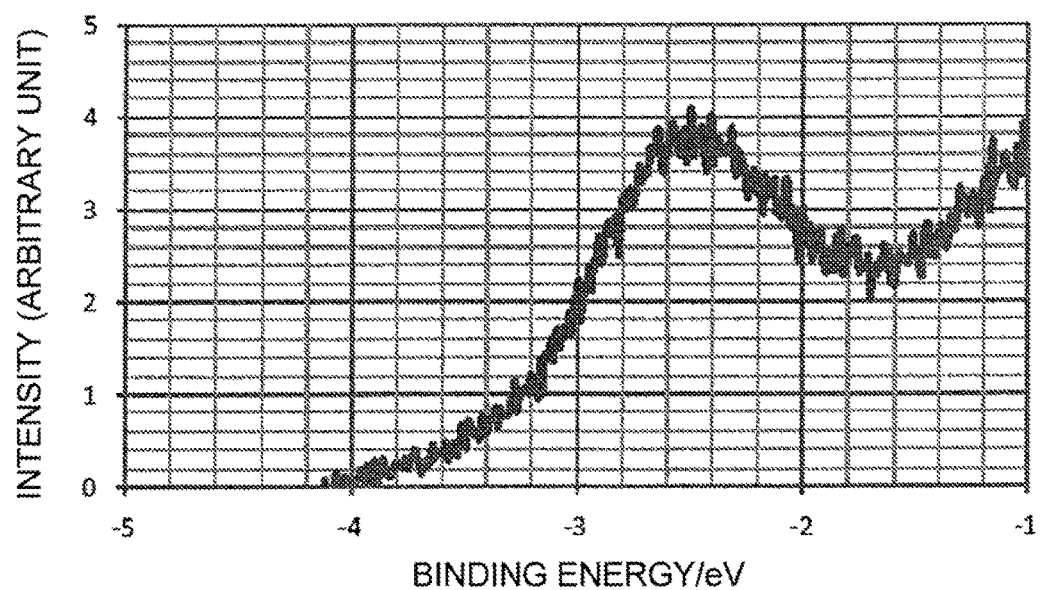
FIG. 9A and FIG. 9B show spectrums of copper phthalocyanine CuPc measured by the device of FIG. 7B and the device of FIG. 7C, respectively.
Figure 9B:
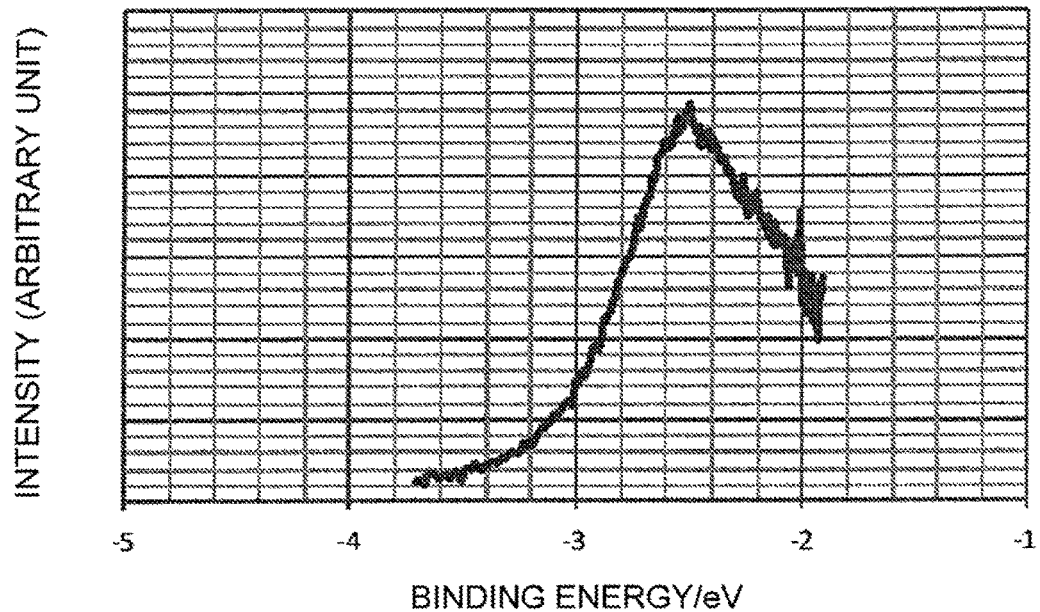

A spectrum obtained as a result of measuring the unoccupied states of the above-mentioned copper phthalocyanine CuPc with the device of FIG. 7B is shown in FIG. 9A, and a spectrum obtained with the device of FIG. 7C is shown in FIG. 9B. The former was measured in the BIS mode, and the latter was measured in the TPE method in which energy of incident electrons is set to 1.18 eV. As is clear from comparison between both the spectrums, a result of sufficient reproducibility can be obtained irrespective of the device configurations and the methods.

Figure 10:
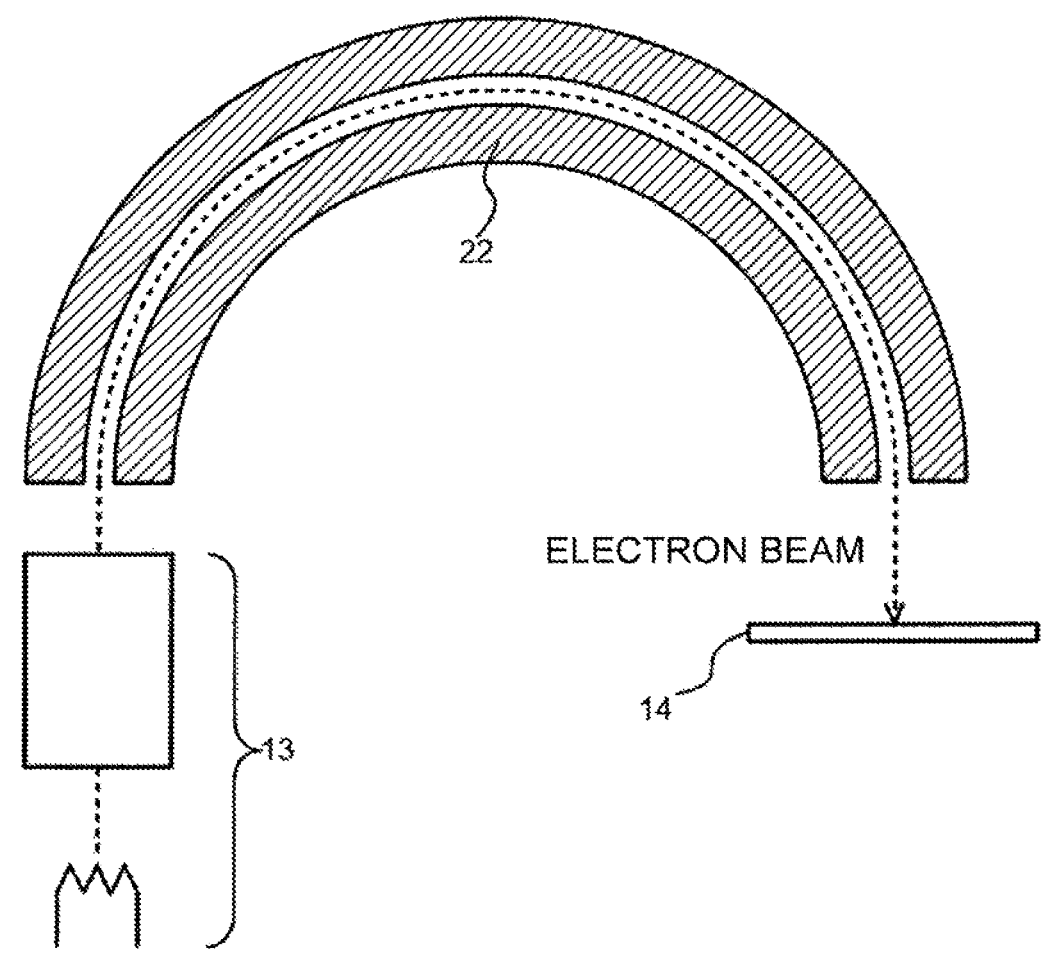
FIG. 10 is a schematic configuration diagram showing a configuration having an electron energy analyser (for example, concentric hemispherical analyser) between an electron gun and a sample.

In both the devices, if the light from the electron gun enters into the photon detector, high sensitivity measurement cannot be implemented. Various measures to reduce such noise are considered. For example, a curved electrode (e.g. concentric hemispherical analyser) 22, which bends an electron track, may be provided in between the electron gun 13 and the sample 14, as shown in FIG. 10 (see Non Patent Literature 8). This prevents the light from the heat cathode 11 (generally made of BaO with 1150 K) of the electron gun 13 from entering into the photon detector 18. When the curved electrode 22 is used, controlling the voltage applied to these electrodes 22 can further uniformize the electron energy entering into the sample 14, so that energy resolution can be enhanced.

Figure 11A:
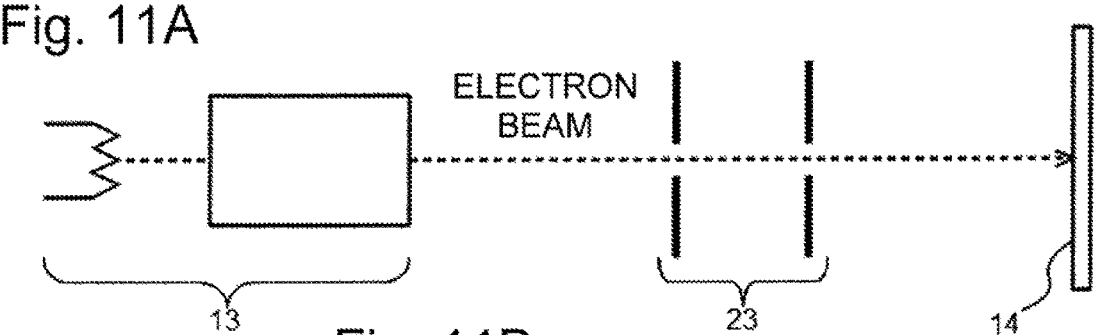
FIG. 11A and FIG. 11B are schematic configuration diagrams showing configurations having a baffle provided between an electron gun and a sample, the baffle being a holed flat baffle and a skimmer baffle, respectively.
Figure 11B:
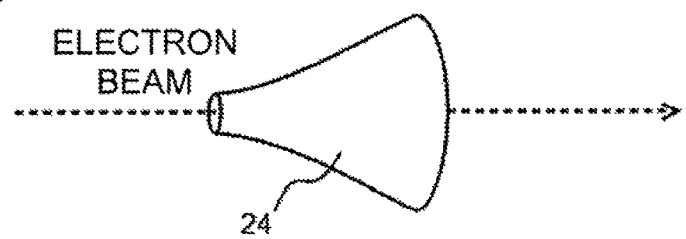

Another method is to provide a baffle between the electron gun 13 and the sample 14. The baffle may be a simple holed plate 23 as shown in FIG. 11A (two or more plates may preferably be placed as shown in FIG. 11A) or may be a skimmer baffle 24 having a diameter gradually increased toward an electron traveling direction as shown in FIG. 11B (see Non Patent Literature 9).

Figure 12A:
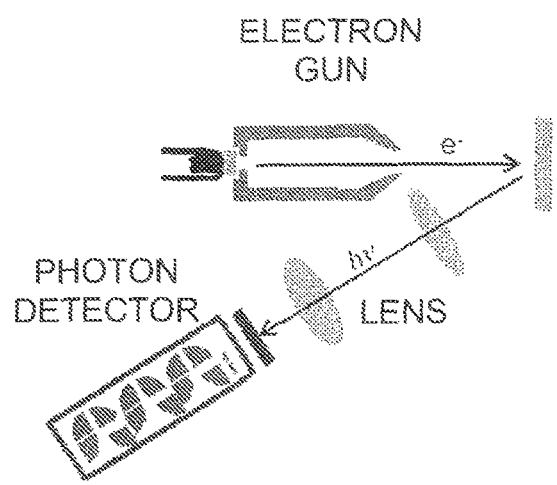
Figure 12B:
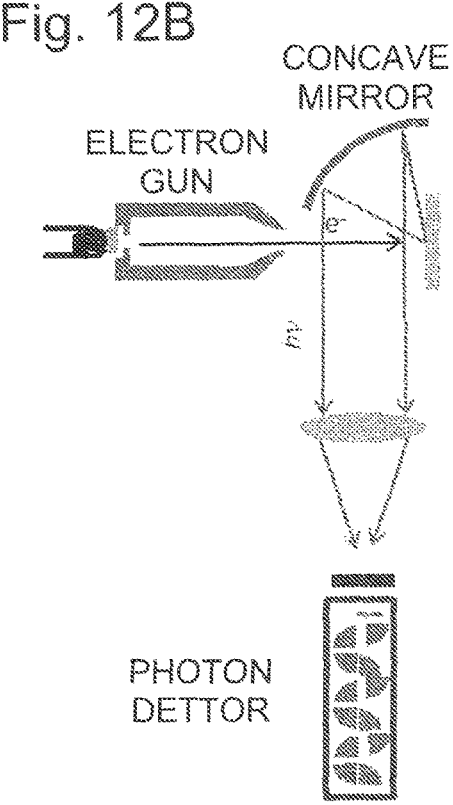
Figure 12C:
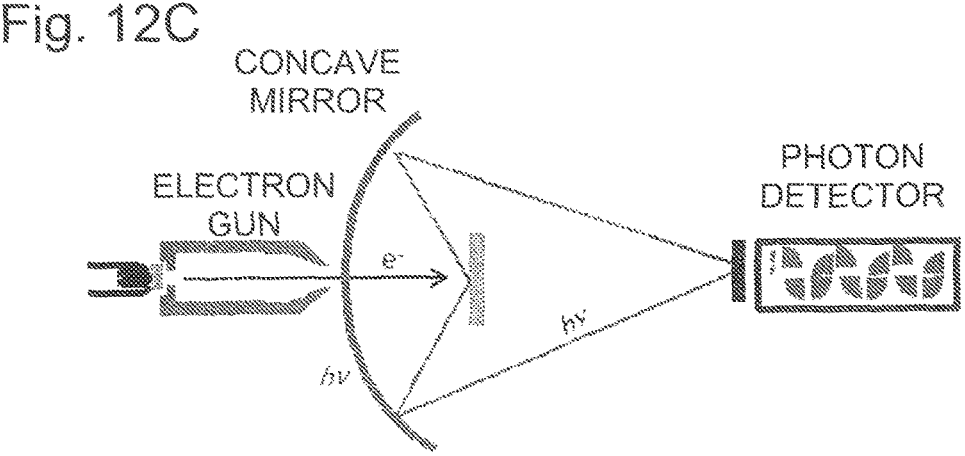

As for the method of collecting visible light and near-ultraviolet light emitted from the sample 14 into the photon detector, not only the methods of the embodiment disclosed but also various kinds of methods can be used. FIG. 12A, FIG. 12B, and FIG. 12C show the device configuration for some of these methods. That is, FIG. 12A shows the device configuration for a method of measuring the light coming from the same surface as the electron entrance surface of the sample 14 (reflection method). FIG. 12B shows the device configuration for a method of collecting the light coming from the electron entrance surface of the sample 14 with use of a concave mirror and detecting the collected light (reflective concave light collection method). FIG. 12C shows the device configuration for a method of collecting the light coming in a direction different from the entering direction with use of a concave mirror and detecting the collected light). In these devices, opaque samples (metals, semiconductors, and the like) can also be measured.

INDUSTRIAL APPLICABILITY

A first field of application of the present invention is organic semiconductor devices. Organic photovoltaic cells in particular are attracting attention as a next generation solar cell which can be mass-produced at low costs. Development of organic semiconductor materials for use in the solar cell are currently being pursued mainly by chemical manufacturers at home and abroad at a fast pace. Organic light emitting diodes are also expected as a low-power and high-intensity flat-panel display device that can be used in place of liquid crystal and LED display devices which are now widely used. In design and development of these organic semiconductor devices, correct electron affinity values of the materials are required. Furthermore, the present invention is applicable not only to the organic semiconductors but also to other organic solids or bio-related substances.

REFERENCE SIGNS LIST

13 . . . Electron Gun
11 . . . Heat Cathode
12 . . . Electron Lens
14 . . . Sample
15 . . . Vacuum Chamber
16 . . . Window
17 . . . Lens
18 . . . Photon Detector
19 . . . Bandpass Filter
20 . . . Photomultiplier
21 . . . Controller
22 . . . Curved Electrode
23 . . . Holed Plate Baffle
24 . . . Skimmer Baffle
EG . . . Electron Gun
S . . . Sample
LS . . . Lens
BPF . . . Bandpass Filter
SP . . . Spectrometer
SE . . . Electroscope Element
LD . . . Linear Sensor
PM . . . Photomultiplier

The invention claimed is:

1. A method for measuring unoccupied states of an organic sample, comprising:
   a) a step of generating an electron beam;
   b) a step of generating an electric potential difference between an electron beam generator and the organic sample by applying a bias voltage to the electron beam generator and/or the organic sample, and irradiating the organic sample with the electron beam whose incident energy with reference to a potential of the organic sample is changed within a range of 0 to 5 eV, the organic sample being degradable above 5 eV;
   c) a step of measuring intensity of light of a predetermined wavelength within a range of 180 to 700 nm included in electromagnetic waves emitted from the organic sample; and
   d) a step of determining unoccupied-states energy of the organic sample based on a spectrum created by the intensity of light with respect to the kinetic energy of the electron beam.

2. The method for measuring unoccupied states of an organic sample according to claim 1, wherein
   in the step of measuring intensity of light, a bandpass filter having a transmission center wavelength of 180 to 700 nm is used.

3. The method for measuring unoccupied states of an organic sample according to claim 1, wherein
   in the step of measuring intensity of light, a spectroscope and an exit slit that perform wavelength scanning in a range of 180 to 700 nm are used.

4. A method for measuring unoccupied states of an organic sample, comprising:
   a) a step of generating an electron beam;
   b) a step of generating an electric potential difference between an electron beam generator and the organic sample by applying a bias voltage to the electron beam generator and/or the organic sample, and irradiating the organic sample with the electron beam whose incident energy with reference to a potential of the organic sample is accelerated with a predetermined energy within a range of 0 to 5 eV, the organic sample being degradable above 5 eV;
   c) a step of spectrally separating light within a range of 180 to 700 nm included in electromagnetic waves emitted from the organic sample, and measuring intensity of each wavelength to generate a spectrum; and
   d) a step of determining unoccupied-states energy of the organic sample based on the spectrum.

5. The method for measuring unoccupied states of an organic sample according to claim 4, wherein
   in the step of generating a spectrum, a spectroscope, an exit slit, and a photon detector are used, and an angular position of the spectroscope is changed to change wavelengths of light that passes through the exit slit so as to generate a spectrum.

6. The method for measuring unoccupied states of an organic sample according to claim 4, wherein
   in the step of generating a spectrum, light from the organic sample is spectrally separated with the spectroscope, and spectrally separated light is measured per wavelength with a linear sensor.

7. A device for measuring unoccupied states of an organic sample, comprising:
   a) an electron beam generator;
   b) an electron beam drive unit for generating an electric potential difference between the electron beam generator and the organic sample by applying a bias voltage to the electron beam generator and/or the organic sample, and irradiating the organic sample with the electron beam whose incident energy with reference to a potential of the organic sample is changed within a range of 1 to 5 eV, the organic sample being degradable above 5 eV;
   c) a light intensity measuring unit for measuring intensity of light of a predetermined wavelength within a range of 180 to 700 nm included in electromagnetic waves emitted from the organic sample; and
   d) an unoccupied states determiner for determining unoccupied-states energy of the organic sample based on a spectrum created by the intensity of light with respect to the kinetic energy of the electron beam.

8. The device for measuring unoccupied states of an organic sample according to claim 7, wherein
   the light intensity measuring unit has a bandpass filter having a transmission center wavelength of 180 to 700 nm and a photon detector that measures intensity of light passing the bandpass filter.

9. The device for measuring unoccupied states of an organic sample according to claim 7, wherein
   the light intensity measuring unit has a spectroscope and an exit slit that perform wavelength scanning in a range of 180 to 700 nm.

10. A device for measuring unoccupied states of an organic sample, comprising:
    a) an electron beam generator;
    b) an electron beam drive unit for generating an electric potential difference between the electron beam generator and the organic sample by applying a bias voltage to the electron beam generator and/or the organic sample, and irradiating the organic sample with the electron beam whose incident energy with reference to a potential of the organic sample is accelerated with a predetermined energy within a range of 0 to 5 eV, the organic sample being degradable above 5 eV;

c) a spectrum generator for generating a spectrum by spectrally separating light within a range of 180 to 700 nm included in electromagnetic waves emitted from the organic sample and measuring intensity of the light as a function of wavelength; and d) an unoccupied states determiner for determining unoccupied-states energy of the organic sample based on the spectrum.

11. The device for measuring unoccupied states of an organic sample according to claim 10, wherein
the spectrum generator includes a spectroscope, a spectroscope drive mechanism that changes an angular position of the spectroscope, an exit slit, and a photon detector.

12. The device for measuring unoccupied states of an organic sample according to claim 10, wherein
the spectrum generator includes a spectroscope and a linear sensor.

13. A method for measuring unoccupied states of an organic sample, comprising:

a) a step of generating an electron beam;

b) a step of irradiating the organic sample with the electron beam whose incident energy with reference to a potential of the organic sample is changed within a range of 0 to 5 eV, the organic sample being degradable above 5 eV;

c) a step of measuring intensity of light of a predetermined wavelength within a range of 180 to 700 nm included in electromagnetic waves emitted from the organic sample, in which the electromagnetic waves are collected by using a lens; and d) a step of determining unoccupied-states energy of the organic sample based on a spectrum created by the intensity of light with respect to the kinetic energy of the electron beam.

14. The method for measuring unoccupied states of an organic sample according to claim 13, wherein
in the step of measuring intensity of light, a bandpass filter having a transmission center wavelength of 180 to 700 nm is used.

15. The method for measuring unoccupied states of an organic sample according to claim 13, wherein
in the step of measuring intensity of light, a spectroscope and an exit slit that perform wavelength scanning in a range of 180 to 700 nm are used.

16. A method for measuring unoccupied states of an organic sample, comprising:

a) a step of generating an electron beam;

b) a step of irradiating the organic sample with the electron beam whose incident energy with reference to a potential of the organic sample is accelerated with a predetermined energy within a range of 0 to 5 eV, the organic sample being degradable above 5 eV;

c) a step of spectrally separating light within a range of 180 to 700 nm included in electromagnetic waves emitted from the organic sample, and measuring intensity of each wavelength to generate a spectrum, in which the electromagnetic waves are collected by using a lens; and d) a step of determining unoccupied-states energy of the organic sample based on the spectrum.

17. The method for measuring unoccupied states of an organic sample according to claim 16, wherein
in the step of generating a spectrum, a spectroscope, an exit slit, and a photon detector are used, and an angular position of the spectroscope is changed to change wavelengths of light that passes through the exit slit so as to generate a spectrum.

18. The method for measuring unoccupied states of an organic sample according to claim 16, wherein
in the step of generating a spectrum, light from the organic sample is spectrally separated with the spectroscope, and spectrally separated light is measured per wavelength with a linear sensor.

19. A device for measuring unoccupied states of an organic sample, comprising:

a) an electron beam generator;

b) an electron beam drive unit for irradiating the organic sample with the electron beam whose incident energy with reference to a potential of the organic sample is changed within a range of 1 to 5 eV, the organic sample being degradable above 5 eV;

c) a light intensity measuring unit for measuring intensity of light of a predetermined wavelength within a range of 180 to 700 nm included in electromagnetic waves emitted from the organic sample, in which the electromagnetic waves are collected by using a lens; and d) an unoccupied states determiner for determining unoccupied-states energy of the organic sample based on a spectrum created by the intensity of light with respect to the kinetic energy of the electron beam.

20. A device for measuring unoccupied states of an organic sample, comprising:

a) an electron beam generator;

b) an electron beam drive unit irradiating the organic sample with the electron beam whose incident energy with reference to a potential of the sample is accelerated with a predetermined energy within a range of 0 to 5 eV, the organic sample being degradable above 5 eV;

c) a spectrum generator for generating a spectrum by spectrally separating light within a range of 180 to 700 nm included in electromagnetic waves emitted from the organic sample and measuring intensity of the light as a function of wavelength, in which the electromagnetic waves are collected by using a lens; and d) an unoccupied states determiner for determining unoccupied-states energy of the organic sample based on the spectrum.

* * * * *